US009006224B2

(12) United States Patent
Marks et al.

(10) Patent No.: US 9,006,224 B2
(45) Date of Patent: Apr. 14, 2015

(54) NEUROENDOCRINE TUMOR TREATMENT

(75) Inventors: Peter Wayne Marks, Woodbridge, CT (US); David Lebwohl, Madison, NJ (US)

(73) Assignee: Novartis AG, Basel (CH)

( * ) Notice: Subject to any disclaimer, the term of this patent is extended or adjusted under 35 U.S.C. 154(b) by 589 days.

(21) Appl. No.: 12/094,173

(22) PCT Filed: Nov. 20, 2006

(86) PCT No.: PCT/EP2006/068656
§ 371 (c)(1),
(2), (4) Date: May 19, 2008

(87) PCT Pub. No.: WO2007/057457
PCT Pub. Date: May 24, 2007

(65) Prior Publication Data
US 2008/0255029 A1    Oct. 16, 2008

(30) Foreign Application Priority Data

Nov. 21, 2005 (GB) .................................. 0523658.3
Jan. 19, 2006 (GB) .................................. 0601082.1
Feb. 10, 2006 (GB) .................................. 0602747.8
Apr. 21, 2006 (GB) .................................. 0607942.0
May 10, 2006 (GB) .................................. 0609272.0
May 18, 2006 (GB) .................................. 0609912.1
Sep. 14, 2006 (EP) .................................... 06120660

(51) Int. Cl.
A61K 31/436    (2006.01)
A61K 38/31     (2006.01)
A61K 45/06     (2006.01)

(52) U.S. Cl.
CPC ............... *A61K 38/31* (2013.01); *A61K 31/436* (2013.01); *A61K 45/06* (2013.01)

(58) Field of Classification Search
CPC .................................................... A61K 31/436
See application file for complete search history.

(56) References Cited

U.S. PATENT DOCUMENTS

| 5,538,739 | A  | 7/1996  | Bodmer et al.      |
| 2002/0183239 | A1 | 12/2002 | Gibbons, Jr. et al. |
| 2002/0183240 | A1 | 12/2002 | Gibbons            |
| 2003/0008923 | A1 | 1/2003  | Dukart et al.      |
| 2004/0176339 | A1 | 9/2004  | Sherman            |
| 2005/0187184 | A1 | 8/2005  | Gibbons, Jr. et al. |

FOREIGN PATENT DOCUMENTS

| EP | 0 462 071     | 12/1991 |
| RU | 2264405 C2    | 11/2005 |
| WO | 97/05167      | 2/1997  |
| WO | 97/47317      | 12/1997 |
| WO | WO02/066019   | 8/2002  |
| WO | 02/080975     | 10/2002 |
| WO | 02/098416     | 12/2002 |
| WO | 03/020266     | 3/2003  |
| WO | WO2004/004644 A2 | 1/2004 |
| WO | 2004/078133   | 9/2004  |
| WO | 2005/082411   | 9/2005  |
| WO | WO2005/080593 A2 | 9/2005 |
| WO | WO2006/065780 | 6/2006  |
| WO | 2006/071966   | 7/2006  |

OTHER PUBLICATIONS

Merck Manuals, Pancreatic endocrine tumors, 2009, pp. 1-4.*
Novartis Data Sheet. Novartis, GEP NE tumors, published online on Apr. 2005, pp. 1-2.*
Arnold et al. Chapter 15 of "Gastrointestinal and Liver Tumors" by Wolfgang Scheppack, 2004, Chapter 15, pp. 195-233.*
Asano Takayuki, et al: "The rapamycin analog CCI-779 is a potent inhibitor of pancreatic cancer cell proliferation", Biochemical and Biophysical Research Communications, 331, May 27, 2005, pp. 295-302.
Boulay Anne, et al: "Antitumor efficacy of intermittent treatment sshedules with the rapamycin derivative RAD001 correlates with prolonged inactivation of ribosomal protein S6 kinase 1 in peripheral blood mononuclear cells", Cancer Research, 64, Jan. 1, 2004, pp. 252-261.
Boulay Anne, et al: "Prolonged effect of the rapamycin derivative RAD001 on p70S6 kinase activity in tumors, skin and peripheral blood lymphocytes derived from a syngeneic rat pancreatic tumor model: correlation with efficacy of intermittent dosing schedules", Proceedings of the American Association for Cancer Research Annual Meeting, 43, 2002, p. 602.
Burns Christiane, et al: "Rapamycin-induced endothelial cell death and tumor vessel thrombosis potentiate cytotoxic therapy against pancreatic cancer"Clinical Cancer Research, vol. 10, Mar. 15, 2004, pp. 2109-2199.
O'Reilly Terence, et al: "In vivo activity of RAD001, an orally active rapamycin derivative in experimental tumor models", Proceedings of the American Association for Cancer Research Annual Meeting, 43, Mar. 2002, p. 71.
Stephan Susann, et al: "Effect of rapamycin alone and in combination with antiangiogenesis therapy in an orthotopic model of human pancreatic cancer", Clinical Cancer Research, vol. 10, 200-10-15, pp. 6993-7000, 2004.
Townsley Carol A., et al: "Evaluation of adverse events experienced by older patients participating in studies of molecularly targeted agents alone or in combination", Cancer Therapy: Clinical, vol. 12, No. 7, Apr. 1, 2006, pp. 2141-2149.
Database Medline: Canobbio L. et al: "Use of long-acting somatostatin analog, lanreotide, in neuro-endocrine tumors." Oncology reports, vol. 1, No. 1 Jan. 1994 p. 129-131.
Hofsli, Eva et al., "Expression of Chromogranin A and Somatostatin Receptors in pancreatic AR42J Cells", Molecular and Cellular Endocrinology, vol. 194, pp. 165-173 2002.
Dorlands Illustrated Medical Dictionary, "Dorlands Illustrated Medical Dictionary", Elsevier Saunders, 2012, Ed. 32nd 955.
The Merck Index; 15th edition; 2013; p. 718.
Hanin et al., "Effect of Interferon-a Treatment . . ."; The Journal of Nuclear Medicine, No. 52, 2011; pp. 580-585.

* cited by examiner

*Primary Examiner* — Samira Jean-Louis
(74) *Attorney, Agent, or Firm* — Gregory Ferraro

(57) ABSTRACT

A method for treating endocrine tumors by administration of an mTOR inhibitor, optionally in combination with another drug.

3 Claims, No Drawings

NEUROENDOCRINE TUMOR TREATMENT

The present invention relates to organic compounds, more specifically to the use of mTOR inhibitors in neuroendocrine tumor treatment.

An mTOR inhibitor as used herein is a compound which targets intracellular mTOR ("mammalian Target of rapamycin"). mTOR is a family member of phosphatidylinositol 3-kinase (P13-kinase) related kinase. The compound rapamycin and other mTOR inhibitors inhibit mTOR activity via a complex with its intracellular receptor FKBP12 (FK506-binding protein 12). mTOR modulates translation of specific mRNAs via the regulation of the phosphorylation state of several different translation proteins, mainly 4E-PB1, P70S6K (p70S6 kinase 1) and eEF2.

Rapamycin is a known macrolide antibiotic produced by *Streptomyces hygroscopicus* of formula

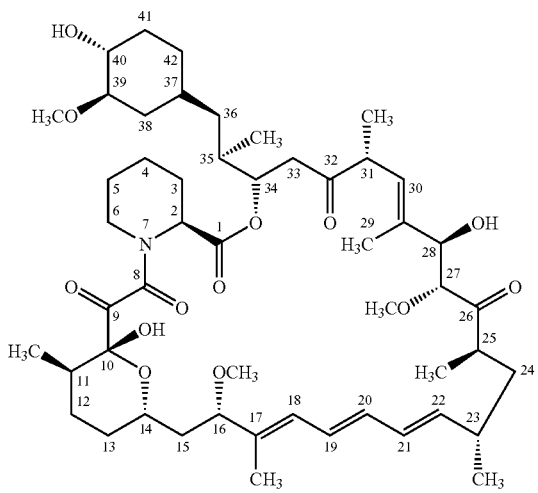

Other mTOR inhibitors include rapamycin derivatives, for example including rapamycin substituted in position 40 and/or 16 and/or 32.

Examples of other mTOR inhibitors include 40-O-alkyl-rapamycin derivatives, e.g. 40-O-hydroxyalkyl-rapamycin derivatives, for example 40-O-(2-hydroxy)-ethyl-rapamycin (everolimus),
rapamycin derivatives which are substituted in 40 position by heterocyclyl, e.g. 40-epi-(tetrazolyl)-rapamycin (also known as ABT578),
32-deoxo-rapamycin derivatives and 32-hydroxy-rapamycin derivatives, such as 32-deoxorapamycin,
16-O-substituted rapamycin derivatives such as 16-pent-2-ynyloxy-32-deoxorapamycin, 16-pent-2-ynyloxy-32(S or R)-dihydro-rapamycin, or 16-pent-2-ynyloxy-32(S or R)-dihydro-40-O-(2-hydroxyethyl)-rapamycin,
rapamycin derivatives which are acylated at the oxygen in position 40, e.g. 40-[3-hydroxy-2-(hydroxy-methyl)-2-methylpropanoate]-rapamycin (also known as CCI779 or temsirolimus),
rapamycin derivatives (also sometimes designated as rapalogs) as disclosed in WO9802441 or WO0114387, e.g. including AP23573, such as 40-O-dimethylphosphinyl-rapamycin, compounds disclosed under the name biolimus (biolimus A9), including 40-O-(2-ethoxy)ethyl-rapamycin, and compounds disclosed under the name TAFA-93, AP23464, AP23675 or AP23841; or mTOR inhibitors as e.g. disclosed in WO2004101583, WO9205179, WO9402136, WO9402385 and WO9613273.

Preferred mTOR inhibitors include
rapamycin, and/or
40-O-(2-hydroxyethyl)-rapamycin, and/or
32-deoxorapamycin, and/or
16-pent-2-ynyloxy-32-deoxorapamycin, and/or
16-pent-2-ynyloxy-32 (S or R)-dihydro-rapamycin, and/or
16-pent-2-ynyloxy-32 (S or R)-dihydro-40-O-(2-hydroxyethyl)-rapamycin, and/or
40-[3-hydroxy-2-(hydroxy-methyl)-2-methylpropanoate]-rapamycin (also known as CCI779) and/or
40-epi-(tetrazolyl)-rapamycin (also known as ABT578), and/or
the so-called rapalogs, e.g. as disclosed in WO9802441, WO0114387 and WO0364383, AP23573, AP23464, AP23675 or AP23841, e.g. AP23573, and/or
compounds disclosed under the name TAFA-93, and/or
compounds disclosed under the name biolimus.

More preferably an mTOR inhibitor is selected from the group consisting of rapamycin, and/or
40-O-(2-hydroxyethyl)-rapamycin, and/or
32-deoxorapamycin, and/or
16-pent-2-ynyloxy-32-deoxorapamycin, and/or
16-pent-2-ynyloxy-32 (S or R)-dihydro-rapamycin, and/or
16-pent-2-ynyloxy-32 (S or R)-dihydro-40-O-(2-hydroxyethyl)-rapamycin, and/or
40-[3-hydroxy-2-(hydroxy-methyl)-2-methylpropanoate]-rapamycin (also known as CCI779) and/or
40-epi-(tetrazolyl)-rapamycin (also known as ABT578), and/or
AP23573,
such as 40-O-(2-hydroxyethyl)-rapamycin.

mTOR inhibitors, on the basis of observed activity, have been found to be useful e.g. as immunosuppressant, e.g. in the treatment of acute allograft rejection and have additionally potent antiproliferative properties which make them useful for cancer chemotherapy, particularly for the treatment of solid tumors, especially of advanced solid tumors.

Endocrine, e.g. neuroendocrine tumors (NETs), are found in the endocrine system. Carcinoid tumors, are a special type of tumor, generally classified as endocrine tumors. Carcinoid tumors belong to the family of neuroendocrine tumors which derive from the neuroendocrine cell system. In the intestinal tract, these tumors develop deep in the mucosa, growing slowly and extending into the underlying submucosa and mucosal surface. This results in the formation of small firm nodules, which bulge into the intestinal lumen. Pancreatic neuroendocrine tumors (islet cell tumors), which were formerly classified as APUDomas (tumors of the amine precursor uptake and decarboxylation system), comprise less than half of all neuroendicrine tumors and only 1-2% of all pancreatic tumors. Pancreatic NETs can arise either in the pancreas (insulinomas, glucagonomas, nonfunctioning pancreatic NETs, pancreatic NETs causing hypercalcemia) or at both pancreatic and extrapancreatic sites (gastrinomas, VIPomas, somatostatinomas, GRFomas). The hormones secreted by pancreatic NETs depend upon the cell of origin and are physiologically involved in a network of autocrine, paracrine, endocrine and neurotransmitter communication. While hormone secretion is not observed in all cases of pancreatic NET, the apparently "nonfunctioning" (i.e., non-secreting) pancreatic NETs tend to be more aggressive and present with symptoms of tumor bulk (see e.g. Barakat et al, Endocrine-related cancer 2004; 11:1-18 and Tomassetti et al, Ann Oncol 2001; 12(Suppl 2): S95-S99).

All pancreatic NETs, with the exception of 90% of insulinomas, have long-term metastatic potential. Most are overtly malignant at the time of diagnosis, and 60% or more present with liver metastases. The most common cause of death from pancreatic NET is hepatic failure (Warner R R P, Gastroenterology 2005; 128:1668-16842005).

In a recent review, the 5-year survival rate in a series of 83 consecutive patients with pancreatic NETs has been reported to be 55.3% which points to an unmet medical need for continued treatment in patients with pancreatic NETs whose disease has progressed following 1 or more courses of chemotherapy.

Carcinoid tumors have historically been classified, according to their point of origin in embryonic development, as arising from the foregut (e.g., bronchial, pulmonary or gastric carcinoid), midgut (e.g., small intestine or appendiceal carcinoid), or hindgut (e.g., rectal carcinoid), see e.g. Kulke M., Cancer Treatment Reviews 2003; 29:363-370.

Primary foregut tumors are confined to the thymus, lung, stomach, and duodenum. Midgut carcinoids are located in the distal ileum, cecum, and proximal colon. One interesting subset of this group is appendiceal carcinoids, which are often benign and rarely give rise to metastatic disease. The midgut carcinoids dominate the malignant carcinoid tumors, particularly when the carcinoid syndrome is present.

The hindgut tumors are primarily located in the distal colon and rectum.

Data suggest that the incidence of pulmonary and gastric carcinoid has increased in the past two decades.

According to histopathologic criteria, carcinoids can be divided into typical (TC) and atypical (AC) carcinoids. Carcinoids can be placed in a spectrum of neuroendocrine tumors, ranging from low-grade malignant TC to intermediate AC to high-grade large-cell neuroendocrine carcinoma and small-cell lung carcinoma.

Carcinoid lung tumors e.g. include neuroendocrine carcinoma, Kulchitsky cell carcinoma (KCC), bronchial carcinoid tumors, bronchial adenomas, typical carcinoids, atypical carcinoids, carcinoid syndrome, small-cell carcinomas, Kulchitsky cells, argentaffin cells, pulmonary carcinoids, neuroendocrine lung tumors, (primary) pulmonary neoplasms, bronchopulmonary carcinoid tumors, lung neoplasms, lung cancers, pulmonary cancers, intrabronchial mass.

Bronchial carcinoid tumors may originate from the neurosecretory cells of bronchial mucosa and were previously classified as bronchial adenomas. Bronchial carcinoids are now classed as low-grade malignant neoplasms because of their potential to cause local invasion, their tendency for local recurrence, and their occasional metastases to extrathoracic sites.

Bronchial carcinoids belong to a group of neuroendocrine tumors, which cover a range of tumors ranging from bronchial carcinoid at one of the spectrum, with a small cell carcinoma, or possibly large cell neuroendocrine tumors at the other end. They demonstrate a wide range of clinical and biologic behaviors, including the potential to synthesize and secrete peptide hormones and neuroamines, particularly adrenocorticotropic hormone (ACTH), serotonin, somatostatin, and bradykinin.

Bronchial carcinoid tumors may arise from Kulchitsky cells (argentaffin cells) within the bronchial mucosa. The predominant distribution of cells are believed to occur at the bifurcation of the lobar bronchi. These cells are neurosecretory cells, which belong to the amine precursor uptake and decarboxylation (APUD) system. They have the capacity to synthesize serotonin (5-hydroxytryptamine), 5-hydroxytryptophan, ACTH, norepinephrine, bombesin, calcitonin, antidiuretic hormone (ADH), and bradykinin.

Large-cell neuroendocrine carcinoma of the lung is a newly recognized clinicopathologic entity, which is distinct from small-cell carcinoma and has a poor prognosis.

Typical carcinoid tumors of the lung represent the most well differentiated and least biologically aggressive type of pulmonary neuroendocrine tumor. These tumors characteristically grow slowly and tend to metastasize infrequently. Atypical carcinoid tumors have a more aggressive histologic and clinical picture. They metastasize at a considerably higher rate than do typical carcinoid tumors. Carcinoid syndrome has been reported in association with very large bronchopulmonary carcinoid tumors or in the presence of metastatic disease. It is noted much less frequently in association with carcinoids of pulmonary origin than those originating within the gastrointestinal tract. Endocrine syndromes found in association with small cell carcinoma of the lung are found less commonly with carcinoid tumors of the lung; however, some endocrine abnormalities have been attributed to both typical and atypical pulmonary carcinoid tumors.

Carcinoid tumors of the GI tract may display an aggressive biology similar to that of adenocarcinomas, particularly when they are located in the colon, stomach, and small intestine, see e.g. Modlin I M et al, Gastroenterology 2005; 128:1717-1751. For small-intestinal carcinoids, which are the most frequent cause of carcinoid syndrome due to metastatic disease in the liver, the incidence of metastasis increases proportionally with the size of the primary tumor (Tomassetti et al 2001, ibidem).

The incidence and survival data available suggest that clinical trials of new anticancer agents in patients with midgut carcinoid tumors may provide the opportunity to address an unmet medical need in a growing segment of the population of patients with carcinoids.

Carcinoid syndrome is caused by hypersecretion of numerous hormone products by the tumor cells, including kinins, prostaglandins, substance P, gastrin, corticotrophin and chromogranin A (see e.g. Davis et al, Gynecology & Obstetrics 1973; 137:637-644). Various endocrine or neuroendocrine syndromes can be initial clinical manifestations of either typical or atypical pulmonary carcinoid tumors. Carcinoid syndrome, hypercortisolism and Cushing syndrome, inappropriate secretion of ADH, increased pigmentation secondary to excess MSH, and ectopic insulin production resulting in hypoglycemia are some of the endocrinopathies that can be produced by a pulmonary carcinoid tumor in a patient who is otherwise asymptomatic.

The most common symptoms are hemoptysis, cough, recurrent pulmonary infection, fever, chest discomfort and chest pain, unilateral wheezing, and shortness of breath, flushing and diarrhea. Paraneoplastic syndromes are rare and include carcinoid syndrome, Cushing's syndrome, and ectopic growth hormone-releasing hormone secretion.

Other less frequent symptoms include cardiac manifestations secondary to fibrosis of the endocardium (Jacobsen M B et al, Eur Heart J 1995; 16:263-268) which may result in valvular regurgitation (valvular heart disease), with varying degrees of heart failure in patients with cardiac manifestations. Wheezing or asthma-like symptoms, pellagra-like skin lesions with hyperkeratosis, abdominal pain, telangiectasias and paroxysmal hypotension are also seen in a number of patients. Patients with pulmonary carcinoid often show symptoms like recurrent pneumonia, cough, hemoptysis or chest pain. The majority of pulmonary carcinoid tumors are in the perihilar area. Ectopic secretion of corticotropin from pulmonary carcinoid tumors may also account for Cushing's syndrome. Early in the course, symptoms are usually episodic and may be provoked by stress, catecholamines, and ingestion of food or alcohol. During acute paroxysms, systolic blood pressure typically falls 20 to 30 mmHg. Endocardial fibrosis can cause valvular heart disease, usually affecting the proximal side of the tricuspid and pulmonary valves and leading to tricuspid insufficiency and secondary right-sided heart failure.

A recent review of chemotherapeutic treatment of carcinoids reports that the sensitivity of these tumors to various cytotoxic drugs is low, and combination does not increase their effectiveness. Based on their review of various combination therapies, including dacarbazine/fluorouracil or 5-fluorouracil/epirubicin, the authors conclude that that they are unable to recommend a specific chemotherapeutic regimen for patients with well-differentiated neuroendocrine malignancies of the GI tract (Arnold R, Rinke A et al, Clinical Gastroenterology 2005; 19(4):649-656). The apparent refractoriness of such tumors to currently available therapies points to an unmet medical need for treatment in this patient population.

As part of the endocrine system that regulates hormones, the pituitary gland controls many of the other glands through secretion. Our "master gland," the pituitary makes some hormones, but also acts as an intermediary between the brain and other endocrine glands. Our hormones and the pituitary gland accomplish many homeostatic and specialized functions, like bone growth and uterine contractions.

Neurons carry messages regarding the production of hormones between the pituitary gland and the hypothalamus. Both are located at the base of the brain, nestled in a rounded part of bone, carefully protected. They are connected by a bunch of neurons called the infundibulum. Together, they work to regulate all the hormones that circulate in the bloodstream, controlling things like growth and hair pigmentation. Hormones are the long-distance messangers that can inform cells when to become active or stay dormant. The pituitary gland controls the thyroid, adrenal glands, ovaries and testes, even though it's only the size of a pea.

There are different parts of the pituitary gland that have selective functions. The posterior lobe, called the neurohypophysis, releases the hormones vasopressin and oxytocin, but doesn't produce them. Vasopressin is an anti-diuretic that controls how the kidneys absorb water. Oxytocin is a special hormone only present during childbirth to speed contractions. The anterior lobe of the pituitary gland is called the adenohypophysis. It produces a variety of hormones, such as prolactin that stimulates lactation in women. Melanocyte spurs the body to produce melanin for skin and hair pigmentation. Follicle-stimulating hormone indicates where and when hair should grow during development. The very important growth hormone controls bone growth to determine height, especially active during adolescence. Hormones control glands as well. The thyroid reacts to thyrotropin, the adrenal glands are stimulated by adrenocorticotropin, and the sex glands are affected by luteinizing hormone. The pituitary gland is responsible for many stages and aspects of our maturation.

Pituitary tumors are in general noncancerous (benign), comprising only 10 percent of brain tumors. However, because of the location of the pituitary gland, at the base of the skull, a pituitary tumor grows upward. And, eventually, many pituitary tumors press against the optic nerves, causing vision problems. Symptoms vary depending upon what type of tumor is growing and what area of the pituitary gland is affected. Pituitary tumors can cause symptoms that are caused by excess production of pituitary hormones and symptoms caused by reduced production of pituitary hormones. Other symptoms may be due to the proximity of these tumors to local brain structures, such as the optic nerves leading to loss of vision. Each individual also experiences symptoms differently, and the symptoms many resemble other conditions or medical problems The most common type of pituitary tumor is called a clinically nonfunctioning tumor, because patients do not have the classic pituitary syndromes from excess hormones, such as in acromegaly. These types of tumors may be detected during an evaluation of an incidental problem. A clinically nonfunctioning tumor may cause hypopituitarism, or an underactive pituitary gland, which may lead to failure of sexual function, reduced sperm production, and cessation of a woman's menstrual period, along with fatigue.

Another common pituitary tumor is called a prolactinoma, a benign tumor that produces the prolactin hormone. Prolactin stimulates breast milk production after childbirth. Women with a prolactinoma may have reduced or absent menstrual cycles along with breast milk production.

An uncommon pituitary tumor causes excess growth hormone production (a hormone necessary for normal childhood growth) resulting in acromegaly. In adults, such tumors lead to excessive somatic growth and multiple systemic, medical consequences. Another uncommon pituitary tumor results in Cushing's disease, a disorder of excess steroid production.

Multiple endocrine neoplasia type 1 (MEN 1) is a relatively uncommon inherited disease. Individuals who inherit the gene for MEN 1 have an increased chance of developing overactivity and enlargement of certain endocrine glands. The endocrine glands most commonly affected by MEN 1 are the parathyroid, pancreas, and pituitary glands. Almost everyone who inherits MEN 1 develops overactivity of the parathyroid glands (hyperparathyroidism) at some stage in their life. The other endocrine glands become overactive less frequently, however, people who inherit MEN 1 will usually develop overactivity in more than one endocrine gland. Overactivity in different endocrine glands may occur simultaneously or at separate times during a persons life. MEN 1 can lead to overactivity and enlargement of the three endocrine glands listed above (the endocrine glands which start with the letter "P"). People who inherit the gene for MEN 1 are predisposed to developing an overactivity in hormone production from the parathyroid glands, pituitary gland and pancreas (that is why physicians will measure hormones in the blood to check for overproduction of each specific hormone). Increased hormone production is usually associated with enlargement of these glands. Endocrine gland enlargement and hormone overproduction does not usually occur in all areas of an endocrine gland at the same point in time. Some parts of overactive endocrine glands grow more rapidly than others, and produce more hormone than other parts of the same gland. The parts of an endocrine gland which grow most rapidly become "lumpy". These lumps are usually benign. Benign lumps in endocrine glands are known as adenomas.

Adenomas are benign (not cancerous), and do not spread to other parts of the body. Pituitary adenomas (pituitary tumors, nervous system tumor) can lead to nerve damage, growth disturbances, and changes in hormonal balance. Symptoms of pituitary adenomas can vary considerably, largely depending on whether or not the tumor is secreting one or more of a variety of hormones. Even if the tumor is not producing any hormones, its location at the base of the brain can cause significant symptoms. Symptoms may e.g. include double or blurred vision, loss of peripheral vision, sudden blindness, headache, dizziness, loss of consciousness, nausea, weakness, unexplained weight changes, amenorrhea, erectile dysfunction in men, decreased sexual desire, especially in men, growth of skull, hands, and feet, deepening of voice, changes in facial appearance (due to changes in facial bones), wider spacing of teeth, joint pain, increased sweating, purple stretch marks on the abdomen, increased hair growth, fat deposits where the neck meets the spine, moodiness or depression, easy bruising, palpitations (rapid or irregular heartbeat), tremor, increased appetite, feeling warm or hot, difficulty falling asleep, anxiousness, frequent bowel movements, lump in the front of the neck (enlarged thyroid).

It was found that mTOR inhibitors may be used for the treatment of such special type of tumors In accordance with the particular findings the present invention provides in several aspects:

1.1 A method for treating endocrine tumors, comprising administering to a subject in need thereof a therapeutically effective amount of an mTOR inhibitor.
1.2 A method for inhibiting growth of endocrine tumors, comprising administering to a subject in need thereof a therapeutical effective amount of an mTOR inhibitor.
1.3 A method for inhibiting or controlling endocrine tumors, comprising administering to a subject in need thereof a therapeutically effective amount of an mTOR inhibitor.
1.4 A method for inducing endocrine tumor regression, e.g. tumor mass reduction, comprising administering to a subject in need thereof a therapeutical effective amount of an mTOR inhibitor.
1.5 A method for treating endocrine tumor invasiveness or symptoms associated with such tumor growth, comprising administering to a subject in need thereof a therapeutically effective amount of an mTOR inhibitor.
1.6 A method for preventing metastatic spread of endocrine tumors or for preventing or inhibiting growth of micrometastasis, comprising administering to a subject in need thereof a therapeutically effective amount of an mTOR inhibitor.
1.7 A method for the treatment of a disorder associated with endocrine tumors, comprising administering to a subject in need thereof a therapeutically effective amount of an mTOR inhibitor.
1.8 The use of an mTOR inhibitor for the manufacture of a medicament for use in any method of 1.1 to 1.7 above.
1.9 A pharmaceutical composition comprising an mTOR inhibitor in association with at least one pharmaceutically acceptable excipient, e.g. appropriate carrier and/or diluent, e.g. including fillers, binders, disintegrants, flow conditioners, lubricants, sugars or sweeteners, fragrances, preservatives, stabilizers, wetting agents and/or emulsifiers, solubilizers, salts for regulating osmotic pressure and/or buffers; for use in any method or use of 1.1 to 1.7 above.

Endocrine tumors as indicated herein e.g. include neuroendocrine tumors, e.g. including carcinoid tumors, pancreatic neuroendocrine tumors and tumors in parathyroid, pancreas, and pituitary glands.

Carcinoid tumors as indicated herein e.g. include typical and atypical carcinoids, ranging from low-grade malignant typical to intermediate atypical to high-grade large-cell neuroendocrine carcinoma and small-cell lung carcinoma; e.g. including carcinoids arising from the foregut e.g., bronchial, pulmonary or gastric carcinoids, e.g. including primary foregut tumors confined to the thymus, lung, stomach, and duodenum; e.g. carcinoid tumors of the GI tract, e.g. located in the colon, stomach or small intestine, e.g. small-intestinal carcinoids, e.g. including midgut, e.g., small intestine or appendiceal carcinoids, e.g. located in the distal ileum, cecum, and proximal colon, or hindgut, e.g., rectal carcinoids.

Carcinoid lung tumors as indicated herein e.g. include neuroendocrine carcinoma, Kulchitsky cell carcinoma (KCC) (Kulchitsky cells, argentaffin cells), bronchial carcinoid tumors, bronchial adenomas, e.g. including bronchial adenomas such as a small cell carcinoma and large cell neuroendocrine tumors, typical carcinoids or atypical carcinoids associated with large bronchopulmonary carcinoid tumors or small-cell carcinomas, pulmonary carcinoids, neuroendocrine lung tumors, large-cell neuroendocrine carcinoma of the lung, (primary) pulmonary neoplasms, bronchopulmonary carcinoid tumors, lung neoplasms, lung cancers, pulmonary cancers, intrabronchial mass.

Pancreatic neuroendocrine tumors as indicated herein e.g. include islet cell tumors, APUDomas, insulinomas, glucagonomas, nonfunctioning pancreatic NETs, pancreatic NETs associated with hypercalcemia, gastrinomas, VIPomas, somatostatinomas, GRFomas.

Endocrine or neuroendocrine tumor symptoms as indicated herein e.g. include hemoptysis, cough, recurrent pulmonary infection, fever, chest discomfort and chest pain, unilateral wheezing, shortness of breath, flushing and diarrhea, endocrine or neuroendocrine syndromes carcinoid syndrome, e.g. including manifestations of either typical or atypical pulmonary carcinoid tumors, Cushing's syndrome, inappropriate secretion of ADH, increased pigmentation secondary to excess MSH, and ectopic insulin production resulting in hypoglycemia, ectopic growth hormone-releasing hormone secretion, ectopic secretion of corticotropin, cardiac manifestations secondary to fibrosis of the endocardium (endocardial fibrosis), valvular regurgitation (valvular heart disease), tricuspid insufficiency, secondary right-sided heart failure, wheezing or asthma-like symptoms, pellagra-like skin lesions with hyperkeratosis, abdominal pain, telangiectasias and paroxysmal hypotension, recurrent pneumonia, cough, chest pain.

Tumors in parathyroid, pancreas and pituitary glands as indicated herein, e.g. include pituitary tumors, nervous system tumor, such as adenomas, multiple endocrine neoplasia type 1 (MEN 1).

Pituitary tumor symptoms as indicated herein include symptoms that are associated with excess production of pituitary hormones and symptoms caused by reduced production of pituitary hormones, loss of vision, clinically nonfunctioning tumor, e.g. associated with hypopituitarism underactive pituitary gland, e.g. associated with failure of sexual function, reduced sperm production, and cessation of a woman's menstrual period, along with fatigue, prolactinoma, a benign tumor that produces the prolactin hormone, acromegaly, e.g. associated with excessive somatic growth and multiple systemic, medical consequences, Cushing's disease, nerve damage, growth disturbances, changes in hormonal balance, double or blurred vision, loss of peripheral vision, sudden blindness, headache, dizziness, loss of consciousness, nausea, weakness, unexplained weight changes, amenorrhea, erectile dysfunction in men, decreased sexual desire, especially in men, growth of skull, hands, and feet, deepening of voice, changes in facial appearance (due to changes in facial bones), wider spacing of teeth, joint pain, increased sweating, purple stretch marks on the abdomen, increased hair growth, fat deposits where the neck meets the spine, moodiness or depression, easy bruising, palpitations (rapid or irregular heartbeat), tremor, increased appetite, feeling warm or hot, difficulty falling asleep, anxiousness, frequent bowel movements, lump in the front of the neck (enlarged thyroid).

Where hereinbefore and subsequently a tumor, a tumor disease, a carcinoma or a cancer is mentioned, also metastasis in the original organ or tissue and/or in any other location are implied alternatively or in addition, whatever the location of the tumor and/or metastasis is.

Disorders associated with endocrine tumors include endocrine or neuroendocrine tumor symptoms and pituitary tumor symptoms, such as indicated above.

Disorders include diseases.

An mTOR inhibitor may be used, e.g. in any method of 1.1 to 1.8 as described herein alone or in combination with one or more, at least one, second drug substance.

In other aspects the present invention provides 2.1 A combination of an mTOR inhibitor with at least one second drug substance, e.g. for any use as indicated under 1.1 to 1.8 above.

2.2 A pharmaceutical combination comprising an mTOR inhibitor in combination with at least one second drug substance, e.g. for any use as indicated under 1.1 to 1.8 above.

2.3 A pharmaceutical composition comprising an mTOR inhibitor in combination with at least one second drug substance and one or more pharmaceutically acceptable excipient(s), e.g. for any use as indicated under 1.1 to 1.8 above.

2.4 The use of an mTOR inhibitor for the manufacture of a medicament for use in combination with a second drug substance, e.g. for any use as indicated under 1.1 to 1.8 above.

2.5 Any method of 1.1 to 1.8 above comprising co-administering, concomitantly or in sequence, a therapeutically effective amount of an mTOR inhibitor and at least one second drug substance, e.g. in the form of a pharmaceutical combination or composition.

2.6 An mTOR inhibitor in combination with at least one second drug substance for use in the preparation of a medicament, e.g. for use in any method of 1.1 to 1.8 above.

2.7 Any method as indicated under 2.1 to 2.6 above, wherein the mTOR inhibitor is administered intermittently.

Combinations include fixed combinations, in which an mTOR inhibitor and at least one second drug substance are in the same formulation; kits, in which an mTOR inhibitor and at least one second drug substance in separate formulations are provided in the same package, e.g. with instruction for co-administration; and free combinations in which an mTOR inhibitor and at least one second drug substance are packaged separately, but instruction for concomitant or sequential administration are given.

In another aspect the present invention provides 2.8 A pharmaceutical package comprising a first drug substance which is an mTOR inhibitor and at least one second drug substance, beside instructions for combined administration;

2.9 A pharmaceutical package comprising an mTOR inhibitor beside instructions for combined administration with at least one second drug substance;

2.10 A pharmaceutical package comprising at least one second drug substance beside instructions for combined administration with an mTOR inhibitor;

e.g. for use in any method of 1.1 to 1.8 above.

Treatment with combinations according to the present invention may provide improvements compared with single treatment.

In another aspect the present invention provides 2.11 A pharmaceutical combination comprising an amount of an mTOR inhibitor and an amount of a second drug substance, wherein the amounts are appropriate to produce a synergistic therapeutic effect.

2.12—A method for improving the therapeutic utility of a an mTOR inhibitor comprising co-administering, e.g. concomitantly or in sequence, a therapeutically effective amount of an mTOR inhibitor and a second drug substance.

2.13 A method for improving the therapeutic utility of a second drug substance comprising co-administering, e.g. concomitantly or in sequence, a therapeutically effective amount of an mTOR inhibitor and a second drug substance.

e.g. for use in any method of 1.1 to 1.8 above.

In a method of 2.11 to 2.13 above the activity of an mTOR inhibitor or a second drug substance may be enhanced compared with single treatment, e.g. combined treatment may result in synergistic effects or may overcome resistance against an mTOR inhibitor or a chemotherapeutic agent, e.g. when used in any method according to 1.1 to 1.8 as described above.

A (pharmaceutical) combination, e.g. composition as indicated under 2.1 to 2.13 comprises a) a first agent which is an mTOR inhibitor and b) a second drug substance as a co-agent which is a chemotherapeutic agent, e.g. as defined hereinafter or hereinbefore.

Treatment of disorders (diseases) according to the present invention includes prophylaxis (prevention).

For such treatment, the appropriate dosage will, of course, vary depending upon, for example, the chemical nature and the pharmacokinetic data of a compound used, the individual host, the mode of administration and the nature and severity of the conditions being treated. However, in general, for satisfactory results in larger mammals, for example humans, an indicated daily dosage includes a range from about 0.0001 g to about 1.5 g, such as 0.001 g to 1.5 g;

from about 0.001 mg/kg body weight to about 20 mg/kg body weight, such as 0.01 mg/kg body weight to 20 mg/kg body weight, for example administered in divided doses up to four times a day.

In a method, for use or in a combination, pharmaceutical combination or pharmaceutical composition provided by the present invention an mTOR inhibitor, such as rapamycin or rapamycin derivative, may be administered as appropriate, e.g. in dosages which are known for mTOR inhibitors, by any administration route, e.g. enterally, e.g. orally, or parenterally. E.g. everolimus may be administered, e.g. orally, in dosages from 0.1 mg up to 15 mg, such as 0.1 mg to 10 mg. e.g. 0.1 mg, 0.25 mg, 0.5 mg, 0.75 mg, 1 mg, 2.5 mg, 5 mg, or 10 mg, more preferably from 0.5 mg to 10 mg, e.g. in the form of (dispersible) tablets; e.g. comprising everolimus in the form of a solid dispersion; e.g. a weekly dosage may include up to 70 mg, e.g. 10 to 70, such as 30 to 50 mg, depending on the disease being treated. Rapamycin or e.g. temsirolimus may be administered parenterally in similar dosage ranges.

A second drug substance may be administered in combination therapy as appropriate, e.g. according to a method as conventional, e.g. analogously to administration indications given for a specified drug for single treatment.

A second drug substance according to the present invention may be administered by any conventional route, for example enterally, e.g. including nasal, buccal, rectal, oral, administration; parenterally, e.g. including intravenous, intraarterial, intramuscular, intracardiac, subcutaneous, intraosseous infusion, transdermal (diffusion through the intact skin), transmucosal (diffusion through a mucous membrane), inhalational administration; topically; e.g. including epicutaneous, intranasal, intratracheal administration; intraperitoneal (infusion or injection into the peritoneal cavity); epidural (peridural) (injection or infusion into the epidural space); intrathecal (injection or infusion into the cerebrospinal fluid); intravitreal (administration via the eye); or via medical devices, e.g. for local delivery, e.g. stents; e.g. in form of coated or uncoated tablets, capsules, (injectable) solutions, infusion solutions, solid solutions, suspensions, dispersions, solid dispersions; e.g. in the form of ampoules, vials, in the form of creams, gels, pastes, inhaler powder, foams, tinctures, lip sticks, drops, sprays, or in the form of suppositories.

A second drug substance according to the present invention may be administered in the form of a pharmaceutically acceptable salt, or in free form; optionally in the form of a solvate. Pharmaceutical compositions according to the present invention may be manufactured according, e.g. analogously, to a method as conventional, e.g. by mixing, granulating, coating, dissolving or lyophilizing processes. Unit dosage forms may contain, for example, from about 0.1 mg to about 1500 mg, such as 1 mg to about 1000 mg.

Pharmaceutical compositions comprising a combination of the present invention and pharmaceutical compositions comprising a second drug substance as described herein, may be provided as appropriate, e.g. according, e.g. analogously, to a method as conventional, or as described herein for a pharmaceutical composition of the present invention.

By the term "second drug substance" as used herein is meant either an mTOR inhibitor other than the first drug substance or a chemotherapeutic agent other than an mTOR inhibitor, preferably any chemotherapeutic agent other an mTOR inhibitor.

For example, a second drug substance as used herein includes e.g.

an anticancer drug, preferably an anti-endocrine tumor agent,
an anti-inflammatory and/or immunomodulatory and/or antiallergic drug,
a combination of an anticancer drug with an anti-inflammatory and/or immunomodulatory drug and/or antiallergic drug.

A second drug substance also include agents which are useful in the treatment of symptoms associated with carciniod tumors, such as carcinoid associated diarrhea (e.g. cyproheptadine), carcinoid associated wheezing (e.g. bronchodilators), carcinoid associated heart failure (e.g. diuretics, serotonine inhibitors).

In another aspect the present invention provides

3. Any method, combination, pharmaceutical combination, pharmaceutical composition or use as indicated under 1.1 to 1.9 and 2.1 to 2.13 above wherein an mTOR inhibitor is selected from rapamycin or a rapamycin derivative, such as rapamycin, and/or 40-O-(2-hydroxyethyl)-rapamycin (also known as everolimus), and/or
32-deoxorapamycin, and/or
16-pent-2-ynyloxy-32-deoxorapamycin, and/or
16-pent-2-ynyloxy-32 (S or R)-dihydro-rapamycin, and/or
16-pent-2-ynyloxy-32 (S or R)-dihydro-40-0-(2-hydroxyethyl)-rapamycin, and/or
40-[3-hydroxy-2-(hydroxy-methyl)-2-methylpropanoate]-rapamycin (also known as CCI779) and/or
40-epi-(tetrazolyl)-rapamycin (also known as ABT578), and/or
the so-called rapalogs, e.g. as disclosed in WO9802441, WO0114387 and WO0364383, AP23573, AP23464, AP23675 or AP23841, e.g. AP23573, and/or
compounds disclosed under the name TAFA-93, and/or
compounds disclosed under the name biolimus;
e.g. 40-O-(2-hydroxyethyl)-rapamycin (herein also designated as "compound A").

In a preferred aspect the present invention provides any method, combination, pharmaceutical combination, pharmaceutical composition, or use as indicated under 1.1 to 1.9 and 2.1 to 2.13 above for treating neuroendocrine tumors.

In another preferred aspect the present invention provides any method, combination, pharmaceutical combination, pharmaceutical composition, or use as indicated under 1.1 to 1.9 and 2.1 to 2.13 above for treating carcinoid tumors.

In another preferred aspect the present invention any method, combination, pharmaceutical combination, pharmaceutical composition, or use as indicated under 1.1 to 1.9 and 2.1 to 2.13 above for treating pituitary tumors.

Anticancer drugs which are prone to be useful as a combination partner with an mTOR inhibitor, e.g. prone to be useful according to the present invention, e.g. include i. a steroid; e.g. prednisone.
ii. an adenosine-kinase-inhibitor; which targets, decreases or inhibits nucleobase, nucleoside, nucleotide and nucleic acid metabolisms, such as 5-Iodotubercidin, which is also known as 7H-pyrrolo[2,3-d]pyrimidin-4-amine, 5-iodo-7-β-D-ribofuranosyl-(9Cl).
iii. an adjuvant; which enhances the 5-FU-TS bond as well as a compound which targets, decreases or inhibits, alkaline phosphatase, such as leucovorin, levamisole.
iv. an adrenal cortex antagonist; which targets, decreases or inhibits the activity of the adrenal cortex and changes the peripheral metabolism of corticosteroids, resulting in a decrease in 17-hydroxycorticosteroids, such as mitotane.
v. an AKT pathway inhibitor; such as a compound which targets, decreases or inhibits Akt, also known as protein kinase B (PKB), such as deguelin, which is also known as 3H-bis[1]benzopyrano[3,4-b:6',5'-e]pyran-7(7aH)-one, 13,13a-dihydro-9,10-dimethoxy-3,3-dimethyl-, (7aS, 13aS)-(9Cl); and triciribine, which is also known as 1,4,5,6,8-pentaazaacenaphthylen-3-amine, 1,5-dihydro-5-methyl-1-β-D-ribofuranosyl-(9Cl).
vi. an alkylating agent; which causes alkylation of DNA and results in breaks in the DNA molecules as well as cross-linking of the twin strands, thus interfering with DNA replication and transcription of RNA, such as chlorambucil, cyclophosphamide, dacarbazine, lomustine, procarbazine, e.g. in the form of a hydrochloride, thiotepa, melphalan, temozolomide (TEMODAR®), carmustine, ifosfamide, mitomycin, altretamine, busulfan, machlorethamine hydrochloride, nitrosourea (BCNU or Gliadel), streptozocin, estramustine. Cyclophosphamide can be administered, e.g., in the form as it is marketed, e.g., under the trademark CYCLOSTIN®; and ifosfamide as HOLOXAN®.
vii. an angiogenesis inhibitor; which targets, decreases or inhibits the production of new blood vessels, e.g. which targets methionine aminopeptidase-2 (MetAP-2), macrophage inflammatory protein-1 (MIP-1 alpha), CCL5, TGF-beta, lipoxygenase, cyclooxygenase, and topoisomerase, or which indirectly targets p21, p53, CDK2 and collagen synthesis, e.g. including fumagillin, which is known as 2,4,6,8-decatetraenedioic acid, mono[(3R,4S,5S,6R)-5-methoxy-4-[(2R,3R)-2-methyl-3-(3-methyl-2-butenyl)oxiranyl]-1-oxaspiro[2.5]oct-6-yl]ester, (2E,4E,6E,8E)-(9Cl); shikonin, which is also known as 1,4-naphthalenedione, 5,8-dihydroxy-2-[(1R)-1-hydroxy-4-methyl-3-pentenyl]-(9Cl); tranilast, which is also known as benzoic acid, 2-[[3-(3,4-dimethoxyphenyl)-1-oxo-2-propenyl]amino]-(9Cl); ursolic acid; suramin; bengamide or a derivative thereof, thalidomide, TNP-470.
viii. an anti-androgen; which blocks the action of androgens of adrenal and testicular origin which stimulate the growth of normal and malignant prostatic tissue, such as nilutamide; bicalutamide (CASODEX®), which can be formulated, e.g., as disclosed in U.S. Pat. No. 4,636,505.

ix. an anti-estrogen; which antagonizes the effect of estrogens at the estrogen receptor level, e.g. including an aromatase inhibitor, which inhibits the estrogen production, i.e. the conversion of the substrates androstenedione and testosterone to estrone and estradiol, respectively,
e.g. including atamestane, exemestane, formestane, aminoglutethimide, roglethimide, pyridoglutethimide, trilostane, testolactone, ketoconazole, vorozole, fadrozole, anastrozole, letrozole, toremifene; bicalutamide; flutamide; tamoxifen, tamoxifen citrate; tamoxifen; fulvestrant; raloxifene, raloxifene hydrochloride. Tamoxifen may be e.g. administered in the form as it is marketed, e.g., NOLVADEX®; and raloxifene hydrochloride is marketed as EVISTA®. Fulvestrant may be formulated as disclosed in U.S. Pat. No. 4,659, 516 and is marketed as FASLODEX®.

x. an anti-hypercalcemia agent; which is used to treat hypercalcemia, such as gallium (III) nitrate hydrate; and pamidronate disodium.

xi. an antimetabolite; which inhibits or disrupts the synthesis of DNA resulting in cell death, such as 6-mercaptopurine; cytarabine; fludarabine; flexuridine; fluorouracil; 5-fluorouracil (5-FU), floxuridine (5-FUdR), capecitabine; raltitrexed; methotrexate; cladribine; gemcitabine; gemcitabine hydrochloride; thioguanine; 6-thioguanine, hydroxyurea; DNA de-methylating agents, such as 5-azacytidine and decitabine; edatrexate; folic acid antagonists such as pemetrexed. Capecitabine and gemcitabine can be administered e.g. in the marketed form, such as XELODA® and GEMZAR®.

xii. an apoptosis inducer; which induces the normal series of events in a cell that leads to its death, e.g. selectively inducing the X-linked mammalian inhibitor of apoptosis protein XIAP, or e.g. downregulating BCL-xL; such as ethanol, 2-[[3-(2,3-dichlorophenoxy)propyl]amino]-(9Cl); gambogic acid; embelin, which is also known as 2,5-cyclohexadiene-1,4-dione, 2,5-dihydroxy-3-undecyl-(9Cl); arsenic trioxide.

xiii. an aurora kinase inhibitor; which targets, decreases or inhibits later stages of the cell cycle from the G2/M check point all the way through to the mitotic checkpoint and late mitosis; such as binucleine 2, which is also known as methanimidamide, N'-[1-(3-chloro-4-fluorophenyl)-4-cyano-1H-pyrazol-5-yl]-N,N-dimethyl-(9Cl).

xiv. a Bruton's Tyrosine Kinase (BTK) inhibitor; which targets, decreases or inhibits human and murine B cell development; such as terreic acid.

xv. a calcineurin inhibitor; which targets, decreases or inhibits the T cell activation pathway, such as cypermethrin, which is also known as cyclopropanecarboxylic acid, 3-(2,2-dichloroethenyl)-2,2-dimethyl-,cyano(3-phenoxyphenyl) methyl ester (9Cl); deltamethrin, which is also known as cyclopropanecarboxylic aci, 3-(2,2-dibromoethenyl)-2,2-dimethyl-(S)-cyano(3-phenoxyphenyl)methyl ester, (1R, 3R)-(9Cl); fenvalerate, which is also known as benzeneacetic acid, 4-chloro-α-(1-methylethyl)-,cyano(3-phenoxyphenyl)methyl ester (9Cl); and Tyrphostin 8; but excluding cyclosporin or FK506.

xvi. a CaM kinase II inhibitor; which targets, decreases or inhibits CaM kinases; constituting a family of structurally related enzymes that include phosphorylase kinase, myosin light chain kinase, and CaM kinases I-IV; such as 5-isoquinolinesulfonic acid, 4-[(2S)-2-[(5-isoquinolinylsulfonyl)methylamino]-3-oxo-3-(4-phenyl-1-piperazinyl) propyl]phenyl ester (9Cl); benzenesulfonamide, N-[2-[[[3-(4-chlorophenyl)-2-propenyl]methyl]amino]methyl] phenyl]-N-(2-hydroxyethyl)-4-methoxy-(9Cl).

xvii. a CD45 tyrosine phosphatase inhibitor; which targets, decreases or inhibits dephosphorylating regulatory pTyr residues on Src-family protein-tyrosine kinases, which aids in the treatment of a variety of inflammatory and immune disorders; such as phosphonic acid, [[2-(4-bromophenoxy)-5-nitrophenyl]hydroxymethyl]-(9Cl).

xviii. a CDC25 phosphatase inhibitor; which targets, decreases or inhibits overexpressed dephosphorylate cyclin-dependent kinases in tumors; such as 1,4-naphthalenedione, 2,3-bis[(2-hydroyethyl)thio]-(9Cl).

xix. a CHK kinase inhibitor; which targets, decreases or inhibits overexpression of the antiapoptotic protein Bcl-2; such as debromohymenialdisine. Targets of a CHK kinase inhibitor are CHK1 and/or CHK2.

xx. a controlling agent for regulating genistein, olomucine and/or tyrphostins; such as daidzein, which is also known as 4H-1-benzopyran-4-one, 7-hydroxy-3-(4-hydroxyphenyl)-(9Cl); Iso-Olomoucine, and Tyrphostin 1.

xxi. a cyclooxygenase inhibitor; e.g. including Cox-2 inhibitors; which targets, decreases or inhibits the enzyme cox-2 (cyclooxygenase-2); such as 1H-indole-3-acetamide, 1-(4-chlorobenzoyl)-5-methoxy-2-methyl-N-(2-phenylethyl)-(9Cl); 5-alkyl substituted 2-arylaminophenylacetic acid and derivatives, e.g. celecoxib (CELEBREX®), rofecoxib (VIOXX®), etoricoxib, valdecoxib; or a 5-alkyl-2-arylaminophenylacetic acid, e.g., 5-methyl-2-(2'-chloro-6'-fluoroanilino)phenyl acetic acid, lumiracoxib; and celecoxib.

xxii. a cRAF kinase inhibitor; which targets, decreases or inhibits the up-regulation of E-selectin and vascular adhesion molecule-1 induced by TNF; such as 3-(3,5-dibromo-4-hydroxybenzylidene)-5-iodo-1,3-dihydroindol-2-one;
and benzamide, 3-(dimethylamino)-N-[3-[(4-hydroxybenzoyl)amino]-4-methylphenyl]-(9Cl). Raf kinases play an important role as extracellular signal-regulating kinases in cell differentiation, proliferation, and apoptosis. A target of a cRAF kinase inhibitor includes, but is not limited, to RAF1.

xxiii. a cyclin dependent kinase inhibitor; which targets, decreases or inhibits cyclin dependent kinase playing a role in the regulation of the mammalian cell cycle; such as N9-isopropyl-olomoucine; olomoucine; purvalanol B, which is also known as Benzoic acid, 2-chloro-4-[[2-[[(1R)-1-(hydroxymethyl)-2-methylpropyl]amino]-9-(1-methylethyl)-9H-purin-6-yl]amino]-(9Cl); roascovitine; indirubin, which is also known as 2H-indol-2-one, 3-(1,3-dihydro-3-oxo-2H-indol-2-ylidene)-1,3-dihydro-(9Cl); kenpaullone, which is also known as indolo[3,2-d][1]benzazepin-6(5H)-one, 9-bromo-7,12-dihydro-(9Cl); purvalanol A, which is also known as 1-Butanol, 2-[[6-[(3-chlorophenyl)amino]-9-(1-methylethyl)-9H-purin-2-yl] amino]-3-methyl-, (2R)-(9Cl); indirubin-3'-monooxime. Cell cycle progression is regulated by a series of sequential events that include the activation and subsequent inactivation of cyclin dependent kinases (Cdks) and cyclins. Cdks are a group of serine/threonine kinases that form active heterodimeric complexes by binding to their regulatory subunits, cyclins. Examples of targets of a cyclin dependent kinase inhibitor include, but are not limited to, CDK, AHR, CDK1, CDK2, CDK5, CDK4/6, GSK3beta, and ERK.

xxiv. a cysteine protease inhibitor; which targets, decreases or inhibits cystein protease which plays a vital role in mammalian cellular turnover and apotosis; such as 4-morpholinecarboxamide, N-[(1S)-3-fluoro-2-oxo-1-(2-phenyl-ethyl)propyl]amino]-2-oxo-1-(phenylmethyl)ethyl]-(9Cl).

xxv. a DNA intercalator; which binds to DNA and inhibits DNA, RNA, and protein synthesis; such as plicamycin, dactinomycin.

xxvi. a DNA strand breaker; which causes DNA strand scission and results in inhibition of DNA synthesis, inhibition of RNA and protein synthesis; such as bleomycin.

xxvii. an E3 Ligase inhibitor; which targets, decreases or inhibits the E3 ligase which inhibits the transfer of ubiquitin chains to proteins, marking them for degradation in the proteasome; such as N-((3,3,3-trifluoro-2-trifluoromethyl)propionyl)sulfanilamide.

xxviii. an endocrine hormone; which by acting mainly on the pituitary gland causes the suppression of hormones in males, the net effect being a reduction of testosterone to castration levels; in females, both ovarian estrogen and androgen synthesis being inhibited; such as leuprolide; megestrol, megestrol acetate.

xxix. compounds targeting, decreasing or inhibiting the activity of the epidermal growth factor family of receptor tyrosine kinases (EGFR, ErbB2, ErbB3, ErbB4 as homo- or heterodimers), such as compounds, proteins or antibodies which inhibit members of the EGF receptor tyrosine kinase family, e.g. EGF receptor, ErbB2, ErbB3 and ErbB4 or bind to EGF or EGF-related ligands, and are in particular those compounds, proteins or monoclonal antibodies generically and specifically disclosed in WO 9702266, e.g. the compound of ex. 39, EP0564409, WO9903854, EP0520722, EP0566226, EP0787722, EP0837063, U.S. Pat. No. 5,747,498, WO9810767, WO9730034, WO9749688, WO9738983 and, especially, WO9630347, e.g. a compound known as CP 358774, WO9633980, e.g. a compound known as ZD 1839; and WO 9503283, e.g. a compound known as ZM105180, e.g including trastuzumab (HERCEPTIN®), cetuximab, iressa, OSI-774, CI-1033, EKB-569, GW-2016, E1.1, E2.4, E2.5, E6.2, E6.4, E2.11, E6.3 or E7.6.3, 7H-pyrrolo-[2,3-d]pyrimidine derivatives which are e.g. disclosed in WO03013541, erlotinib, gefitinib. Erlotinib can be administered in the form as it is marketed, e.g. TARCEVA®, and gefitinib as IRESSA®, human monoclonal antibodies against the epidermal growth factor receptor including ABX-EGFR.

xxx. an EGFR, PDGFR tyrosine kinase inhibitor; such as EGFR kinase inhibitors including tyrphostin 23, tyrphostin 25, tyrphostin 47, tyrphostin 51 and tyrphostin AG 825; 2-propenamide, 2-cyano-3-(3,4-dihydroxyphenyl)-N-phenyl-(2E)-(9Cl); tyrphostin Ag 1478; lavendustin A; 3-pyridineacetonitrile, α-[(3,5-dichlorophenyl)methylene]-, (αZ)-(9Cl); an example of an EGFR, PDGFR tyrosine kinase inhibitor e.g. includes tyrphostin 46. PDGFR tyrosine kinase inhibitor including tyrphostin 46. Targets of an EGFR kinase inhibitor include guanylyl cyclase (GC-C) HER2, EGFR, PTK and tubulin.

xxxi. a farnesyltransferase inhibitor; which targets, decreases or inhibits the Ras protein; such as a-hydroxyfarnesylphosphonic acid; butanoic acid, 2-[[(2S)-2-[[(2S,3S)-2-[[(2R)-2-amino-3-mercaptopropyl]amino]-3-methylpentyl]oxy]-1-oxo-3-phenylpropyl]amino]-4-(methylsulfonyl)-,1-methylethyl ester, (2S)-(9cl); manumycin A; L-744,832 or DK8G557, tipifarnib (R115777), SCH66336 (lonafarnib), BMS-214662, xxxii. a Flk-1 kinase inhibitor; which targets, decreases or inhibits Flk-1 tyrosine kinase activity; such as 2-propenamide, 2-cyano-3-[4-hydroxy-3,5-bis(1-methylethyl)phe-nyl]-N-(3-phenylpropyl)-(2E)-(9Cl). A target of a Flk-1 kinase inhibitor includes, but is not limited to, KDR.

xxxiii. a Glycogen synthase kinase-3 (GSK3) inhibitor; which targets, decreases or inhibits glycogen synthase kinase-3 (GSK3); such as indirubin-3'-monooxime. Glycogen Synthase Kinase-3 (GSK-3; tau protein kinase I), a highly conserved, ubiquitously expressed serine/threonine protein kinase, is involved in the signal transduction cascades of multiple cellular processes. which is a protein kinase that has been shown to be involved in the regulation of a diverse array of cellular functions, including protein synthesis, cell proliferation, cell differentiation, microtubule assembly/disassembly, and apoptosis.

xxxiv. a histone deacetylase (HDAC) inhibitor; which inhibits the histone deacetylase and which possess anti-proliferative activity; such as compounds disclosed in WO0222577, especially N-hydroxy-3-[4-[[(2-hydroxy-ethyl) [2-(1H-indol-3-yl)ethyl]-amino]methyl]phenyl]-2E-2-propenamide, and N-hydroxy-3-[4-[[[2-(2-methyl-1H-indol-3-yl)-ethyl]-amino]methyl]phenyl]-2E-2-propenamide and pharmaceutically acceptable salts thereof; suberoylanilide hydroxamic acid (SAHA); [4-(2-amino-phenylcarbamoyl)-benzyl]-carbamic acid pyridine-3-ylmethyl ester and derivatives thereof; butyric acid, pyroxamide, trichostatin A, oxamflatin, apicidin, depsipeptide; depudecin; trapoxin, HC toxin, which is also known as cyclo[L-alanyl-D-alanyl-(□S,2S)-□-amino-□-oxooxiraneoctanoyl-D-prolyl] (9Cl); sodium phenylbutyrate, suberoyl bis-hydroxamic acid; Trichostatin A, BMS-27275, pyroxamide, FR-901228, valproic acid.

xxxv. a HSP90 inhibitor; which targets, decreases or inhibits the intrinsic ATPase activity of HSP90; degrades, targets, decreases or inhibits the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, e.g., 17-allylamino,17-demethoxygeldanamycin (17AAG), a geldanamycin derivative; other geldanamycin-related compounds; radicicol and HDAC inhibitors. Other examples of an HSP90 inhibitor include geldanamycin, 17-demethoxy-17-(2-propenylamino)-(9Cl). Potential indirect targets of an HSP90 inhibitor include FLT3, BCR-ABL, CHK1, CYP3A5*3 and/or NQ01*2.

xxxvi. a 1-kappa B-alpha kinase inhibitor (IKK); which targets, decreases or inhibits NF-kappaB, such as 2-propenenitrile, 3-[(4-methylphenyl)sulfonyl]-(2E)-(9Cl).

xxxvii. an insulin receptor tyrosine kinase inhibitor; which modulates the activities of phosphatidylinositol 3-kinase, microtubule-associated protein, and S6 kinases; such as hydroxyl-2-naphthalenylmethylphosphonic acid, LY294002.

xxxviii. a c-Jun N-terminal kinase (JNK) kinase inhibitor; which targets, decreases or inhibits Jun N-terminal kinase; such as pyrazoleanthrone and/or epigallocatechin gallate. Jun N-terminal kinase (JNK), a serine-directed protein kinase, is involved in the phosphorylation and activation of c-Jun and ATF2 and plays a significant role in metabolism, growth, cell differentiation, and apoptosis. A target for a JNK kinase inhibitor includes, but is not limited to, DNMT.

xxxix a microtubule binding agent; which acts by disrupting the microtubular network that is essential for mitotic and interphase cellular function; such as vinblastine, vinblastine sulfate; vinca alkaloids, such as vincristine, vincristine sulfate; vindesine; vinorelbine; taxanes, such as docetaxel; paclitaxel; discodermolides; cochicine, epothilones and derivatives thereof, e.g. epothilone B or a derivative thereof. Paclitaxel is marketed as TAXOL®; docetaxel as TAXOTERE®; vinblastine sulfate as VINBLASTIN R.P®; and vincristine sulfate as FARMISTIN®. Also included are the generic forms of paclitaxel as well as various dosage forms of paclitaxel. Generic forms of paclitaxel include, but are not limited to, betaxolol hydrochloride. Various dosage forms of paclitaxel include, but are not limited to albumin nanoparticle paclitaxel marketed as ABRAXANE®; ONXOL®, CYTOTAX®. Discodermolide can be obtained, e.g., as disclosed in U.S. Pat. No. 5,010,099. Also included are Epotholine derivatives which are disclosed in U.S. Pat. No. 6,194,181, WO98/0121, WO9825929, WO9808849, WO9943653, WO9822461 and WO0031247. Especially preferred are Epotholine A and/or B.

xl. a mitogen-activated protein (MAP) kinase-inhibitor; which targets, decreases or inhibits Mitogen-activated protein, such as benzenesulfonamide, N-[2-[[[3-(4-chlorophenyl)-2-propenyl]methyl]amino]methyl]phenyl]-N-(2-hydroxyethyl)-4-methoxy-(9Cl). The mitogen-activated protein (MAP) kinases are a group of protein serine/threonine kinases that are activated in response to a variety of extracellular stimuli and mediate signal transduction from the cell surface to the nucleus. They regulate several physiological and pathological cellular phenomena, including inflammation, apoptotic cell death, oncogenic transformation, tumor cell invasion, and metastasis.

xli. a MDM2 inhibitor; which targets, decreases or inhibits the interaction of MDM2 and the p53 tumor suppressor; such as trans-4-iodo, 4'-boranyl-chalcone.

xlii. a MEK inhibitor; which targets, decreases or inhibits the kinase activity of MAP kinase MEK; such as Nexavar® (sorafenib tosylate), butanedinitrile, bis[amino[2-aminophenyl)thio]methylene]-(9Cl). A target of a MEK inhibitor includes, but is not limited to ERK. An indirect target of a MEK inhibitor includes, but is not limited to, cyclin D1.

xliii. a matrix metalloproteinase inhibitor (MMP) inhibitor; which targets, decreases or inhibits a class of protease enzyme that selectively catalyze the hydrolysis of polypeptide bonds including the enzymes MMP-2 and MMP-9 that are involved in promoting the loss of tissue structure around tumors and facilitating tumor growth, angiogenesis, and metastasis such as actinonin, which is also known as butanediamide, N-4-hydroxy-N-1-[(1S)-1-[[(2S)-2-(hydroxymethyl)-1-pyrrolidinyl]carbonyl]-2-methylpropyl]-2-pentyl-, (2R)-(9Cl); epigallocatechin gallate; collagen peptidomimetic and non-peptidomimetic inhibitors; tetracycline derivatives, e.g., hydroxamate peptidomimetic inhibitor batimastat; and its orally-bioavailable analogue marimastat, prinomastat, metastat, neovastat, tanomastat, TAA211, BMS-279251, BAY 12-9566, MM1270B or AAJ996. A target of a MMP inhibitor includes, but is not limited to, polypeptide deformylase.

xliv. a NGFR tyrosine-kinase-inhibitor; which targets, decreases or inhibits nerve growth factor dependent p140$^{c\text{-}trk}$ tyrosine phosphorylation; such as tyrphostin AG 879. Targets of a NGFR tyrosine-kinase-inhibitor include, but are not limited to, HER2, FLK1, FAK, TrkA, and/or TrkC. An indirect target inhibits expression of RAF1.

xlv. a p38 MAP kinase inhibitor, including a SAPK2/p38 kinase inhibitor; which targets, decreases or inhibits p38-MAPK, which is a MAPK family member, such as phenol, 4-[4-(4-fluorophenyl)-5-(4-pyridinyl)-1H-imidazol-2-yl]-(9Cl). An example of a a SAPK2/p38 kinase inhibitor includes, but is not limited to, benzamide, 3-(dimethylamino)-N-[3-[(4-hydroxybenzoyl)amino]-4-methylphenyl]-(9Cl). A MAPK family member is a serine/threonine kinase activated by phosphorylation of tyrosine and threonine residues. This kinase is phosphorylated and activated by many cellular stresses and inflammatory stimuli, thought to be involved in the regulation of important cellular responses such as apoptosis and inflammatory reactions.

xlvi. a p56 tyrosine kinase inhibitor; which targets, decreases or inhibits p56 tyrosine kinase, which is an enzyme that is a lymphoid-specific src family tyrosine kinase critical for T-cell development and activation; such as damnacanthal, which is also known as 2-anthracenecarboxaldehyde,9,10-dihydro-3-hydroxy-1 methoxy-9,10-dioxo-(9Cl), Tyrphostin 46. A target of a p56 tyrosine kinase inhibitor includes, but is not limited to, Lck. Lck is associated with the cytoplasmic domains of CD4, CD8 and the beta-chain of the IL-2 receptor, and is thought to be involved in the earliest steps of TCR-mediated T-cell activation.

xlvii. a PDGFR tyrosine kinase inhibitor; targeting, decreasing or inhibiting the activity of the C-kit receptor tyrosine kinases (part of the PDGFR family), such as targeting, decreasing or inhibiting the activity of the c-Kit receptor tyrosine kinase family, especially inhibiting the c-Kit receptor. Examples of targets of a PDGFR tyrosine kinase inhibitor includes, but are not limited to PDGFR, FLT3 and/or c-KIT; such as tyrphostin AG 1296; tyrphostin 9; 1,3-butadiene-1,1,3-tricarbonitrile,2-amino-4-(1H-indol-5-yl)-(9Cl); N-phenyl-2-pyrimidine-amine derivative, e.g. imatinib, IRESSA®. PDGF plays a central role in regulating cell proliferation, chemotaxis, and survival in normal cells as well as in various disease states such as cancer, atherosclerosis, and fibrotic disease. The PDGF family is composed of dimeric isoforms (PDGF-AA, PDGF-BB, PDGF-AB, PDGF-CC, and PDGF-DD), which exert their cellular effects by differentially binding to two receptortyrosine kinases. PDGFR-α and PDGFR-β have molecular masses of ~170 and 180 kDa, respectively.

xlviii. a phosphatidylinositol 3-kinase inhibitor; which targets, decreases or inhibits PI 3-kinase; such as wortmannin, which is also known as 3H-Furo[4,3,2-de]indeno[4,5-h]-2-benzopyran-3,6,9-trione, 11-(acetyloxy)-1,6b,7,8,9a,10,11,11b-octahydro-1-(methoxymethyl)-9a,11b-dimethyl-, (1S,6bR,9aS,11R,11bR)-(9Cl); 8-phenyl-2-(morpholin-4-yl)-chromen-4-one; quercetin, quercetin dihydrate. PI 3-kinase activity has been shown to increase in response to a number of hormonal and growth factor stimuli, including insulin, platelet-derived growth factor, insulin-like growth factor, epidermal growth factor, colony-stimulating factor, and hepatocyte growth factor, and has been implicated in processes related to cellular growth and transformation. An example of a target of a phosphatidylinositol 3-kinase inhibitor includes, but is not limited to, Pi3K.

xlix. a phosphatase inhibitor; which targets, decreases or inhibits phosphatase; such as cantharidic acid; cantharidin; and L-leucinamide, N-[4-(2-carboxyethenyl)benzoyl]glycyl-L-α-glutamyl-(E)-(9Cl). Phosphatases remove the phosphoryl group and restore the protein to its original dephosphorylated state. Hence, the phosphorylation-dephosphorylation cycle can be regarded as a molecular "on-off" switch.

l. platinum agent; which contains platinum and inhibit DNA synthesis by forming interstrand and intrastrand crosslinking of DNA molecules; such as carboplatin; cisplatin; oxaliplatin; cisplatinum; satraplatin and platinum agents such as ZD0473. Carboplatin can be administered, e.g., in the form as it is marketed, e.g. CARBOPLAT®; and oxaliplatin as ELOXATIN®.

li. a protein phosphatase inhibitor, including a PP1 and PP2 inhibitor and a tyrosine phosphatase inhibitor; which targets, decreases or inhibits protein phosphatase. Examples of a PP1 and PP2A inhibitor include cantharidic acid and/or cantharidin. Examples of a tyrosine phosphatase inhibitor include, but are not limited to, L-P-bromotetramisole oxalate; 2(5H)-furanone,4-hydroxy-5-(hydroxymethyl)-3-(1-oxohexadecyl)-, (5R)-(9Cl); and benzylphosphonic acid.

The term "a PP1 or PP2 inhibitor", as used herein, relates to a compound which targets, decreases or inhibits Ser/Thr protein phosphatases. Type I phosphatases, which include PP1, can be inhibited by two heat-stable proteins known as Inhibitor-1 (I-1) and Inhibitor-2 (I-2). They preferentially dephosphorylate a subunit of phosphorylase kinase. Type II phosphatases are subdivided into spontaneously active (PP2A), $CA^{2+}$-dependent (PP2B), and $Mg^{2+}$-dependent (PP2C) classes of phosphatases.

The term "tyrosine phosphatase inhibitor", as used here, relates to a compounds which targets, decreases or inhibits tyrosine phosphatase. Protein tyrosine phosphatases (PTPs) are relatively recent additions to the phosphatase family. They remove phosphate groups from phosphorylated tyrosine residues of proteins. PTPs display diverse structural features and play important roles in the regulation of cell proliferation, differentiation, cell adhesion and motility, and cytoskeletal function. Examples of targets of a tyrosine phosphatase inhibitor include, but are not limited to, alkaline phosphatase (ALP), heparanase, PTPase, and/or prostatic acid phosphatase.

lii. a PKC inhibitor and a PKC delta kinase inhibitor: The term "a PKC inhibitor", as used herein, relates to a compound which targets, decreases or inhibits protein kinase C as well as its isozymes. Protein kinase C (PKC), a ubiquitous, phospholipid-dependent enzyme, is involved in signal transduction associated with cell proliferation, differentiation, and apoptosis. Examples of a target of a PKC inhibitor include, but are not limited to, MAPK and/or NF-kappaB. Examples of a PKC inhibitor include, but are not limited to, 1-H-pyrrolo-2,5-dione,3-[1-[3-(dimethylamino)propyl]-1H-indol-3-yl]-4-(1H-indol-3-yl)-(9Cl); bisindolylmaleimide IX; sphingosine, which is known as 4-octadecene-1,3-diol, 2-amino-, (2S,3R,4E)-(9Cl); staurosporine, which is known as 9,13-Epoxy-1H,9H-diindolo[1,2,3-gh:3',2',1'-lm]pyrrolo[3,4-j][1,7]benzodiazonin-1-one, staurosporine derivatives such as disclosed in EP0296110, e.g. midostaurin; 2,3,10,11,12,13-hexahydro-10-methoxy-9-methyl-11-(methylamino)-, (9S,10R,11R,13R)-(9Cl); tyrphostin 51; and hypericin, which is also known as phenanthro[1,10,9,8-opqra]perylene-7,14-dione, 1,3,4,6,8,13-hexahydroxy-10,11-dimethyl-, stereoisomer (6Cl,7Cl, 8Cl,9Cl), UCN-01,safingol, BAY 43-9006, bryostatin 1, perifosine; llmofosine; RO 318220 and RO 320432; GO 6976; Isis 3521; LY333531/LY379196. The term "a PKC delta kinase inhibitor", as used herein, relates to a compound which targets, decreases or inhibits the delta isozymes of PKC. The delta isozyme is a conventional PKC isozymes and is $Ca^{2+}$-dependent. An example of a PKC delta kinase inhibitor includes, but is not limited to, Rottlerin, which is also known as 2-Propen-1-one, 1-[6-[(3-acetyl-2,4,6-trihydroxy-5-methylphenyl)methyl]-5,7-dihydroxy-2,2-dimethyl-2H-1-benzopyran-8-yl]-3-phenyl-, (2E)-(9Cl).

liii. a polyamine synthesis inhibitor; which targets, decreases or inhibits polyamines spermidine; such as DMFO, which is also known as (−)-2-difluoromethylornithin; N1, N12-diethylspermine 4HCl. The polyamines spermidine and spermine are of vital importance for cell proliferation, although their precise mechanism of action is unclear. Tumor cells have an altered polyamine homeostasis reflected by increased activity of biosynthetic enzymes and elevated polyamine pools.

liv. a proteosome inhibitor; which targets, decreases or inhibits proteasome, such as aclacinomycin A; gliotoxin; PS-341; MLN 341; bortezomib; velcade. Examples of targets of a proteosome inhibitor include, but are not limited to, O(2)(−)-generating NADPH oxidase, NF-kappaB, and/or farnesyltransferase, geranyltransferase I.

lv. a PTP1B inhibitor; which targets, decreases or inhibits PTP1B, a protein tyrosine kinase inhibitor; such as L-leucinamide, N-[4-(2-carboxyethenyl)benzoyl]glycyl-L-α-glutamyl-, (E)-(9Cl).

lvi. a protein tyrosine kinase inhibitor including a SRC family tyrosine kinase inhibitor; a Syk tyrosine kinase inhibitor; and a JAK-2 and/or JAK-3 tyrosine kinase inhibitor; The term "a protein tyrosine kinase inhibitor", as used herein, relates to a compound which targets, decreases or inhibits protein tyrosine kinases. Protein tyrosine kinases (PTKs) play a key role in the regulation of cell proliferation, differentiation, metabolism, migration, and survival. They are classified as receptor PTKs and non-receptor PTKs. Receptor PTKs contain a single polypeptide chain with a transmembrane segment. The extracellular end of this segment contains a high affinity ligand-binding domain, while the cytoplasmic end comprises the catalytic core and the regulatory sequences. Examples of targets of a tyrosine kinase inhibitor include, but are not limited to, ERK1, ERK2, Bruton's tyrosine kinase (Btk), JAK2, ERK ½, PDGFR, and/or FLT3. Examples of indirect targets include, but are not limited to, TNFalpha, NO, PGE2, IRAK, iNOS, ICAM-1, and/or E-selectin. Examples of a tyrosine kinase inhibitor include, but are not limited to, tyrphostin AG 126; tyrphostin Ag 1288; tyrphostin Ag 1295; geldanamycin; and genistein.

Non-receptor tyrosine kinases include members of the Src, Tec, JAK, Fes, Abl, FAK, Csk, and Syk families. They are located in the cytoplasm as well as in the nucleus. They exhibit distinct kinase regulation, substrate phosphorylation, and function. Deregulation of these kinases has also been linked to several human diseases.

The term "a SRC family tyrosine kinase inhibitor", as used herein, relates to a compound which targets, decreases or inhibits SRC. Examples of a SRC family tyrosine kinase inhibitor include, but are not limited to, PP1, which is also known as 1H-pyrazolo[3,4-d]pyrimidin-4-amine, 1-(1,1-dimethylethyl)-3-(1-naphthalenyl)-(9Cl); and PP2, which is also known as 1H-Pyrazolo[3,4-d]pyrimidin-4-amine, 3-(4-chlorophenyl)-1-(1,1-dimethylethyl)-(9Cl).

The term "a Syk tyrosine kinase inhibitor", as used herein, relates to a compound which targets, decreases or inhibits Syk. Examples of targets for a Syk tyrosine kinase inhibitor include, but are not limited to, Syk, STAT3, and/or STAT5. An example of a Syk tyrosine kinase inhibitor includes, but is not limited to, piceatannol, which is also known as 1,2-benzenediol, 4-[(1E)-2-(3, 5-dihydroxyphenyl)ethenyl]-(9Cl).

The term "a Janus (JAK-2 and/or JAK-3) tyrosine kinase inhibitor", as used herein, relates to a compound which targets, decreases or inhibits janus tyrosine kinase. Janus tyrosine kinase inhibitor are shown anti-leukemic agents with anti-thrombotic, anti-allergic and immunosuppressive properties. Targets of a JAK-2 and/or JAK-3 tyrosine kinase inhibitor include, but are not limited to, JAK2, JAK3, STAT3. An indirect target of an JAK-2 and/or JAK-3 tyrosine kinase inhibitor includes, but is not limited to CDK2. Examples of a JAK-2 and/or JAK-3 tyrosine kinase inhibitor include, but are not limited to, Tyrphostin AG 490; and 2-naphthyl vinyl ketone. Compounds which target, decrease or inhibit the activity of c-Abl family members and their gene fusion products, e.g. include PD180970 AG957; or NSC 680410.

lvii. a retinoid; which target, decrease or inhibit retinoid dependent receptors; such as isotretinoin, tretinoin.

lviii. a RNA polymerase II elongation inhibitor; which targets, decreases or inhibits insulin-stimulated nuclear and cytosolic p70S6 kinase in CHO cells; targets, decreases or inhibits RNA polymerase II transcription, which may be dependent on casein kinase II; and targets, decreases or inhibits germinal vesicle breakdown in bovine oocytes; such as 5,6-dichloro-1-beta-D-ribofuranosylbenzimidazole.

lvix. a serine/threonine kinase inhibitor; which inhibits serine/threonine kinases; such as 2-aminopurine, also known as 1H-purin-2-amine (9Cl). An example of a target of a serine/threonine kinase inhibitor includes, but is not limited to, dsRNA-dependent protein kinase (PKR). Examples of indirect targets of a serine/threonine kinase inhibitor include, but are not limited to, MCP-1, NF-kappaB, eIF2alpha, COX2, RANTES, IL8, CYP2A5, IGF-1, CYP2B1, CYP2B2, CYP2H1, ALAS-1, HIF-1, erythropoietin, and/or CYP1A1.

lx. a sterol biosynthesis inhibitor; which inhibits the biosynthesis of sterols such as cholesterol; such as terbinadine. Examples of targets for a sterol biosynthesis inhibitor include, but are not limited to, squalene epoxidase, and CYP2D6.

lxi. a topoisomerase inhibitor; including a topoisomerase I inhibitor and a topoisomerase II inhibitor. Examples of a topoisomerase I inhibitor include, but are not limited to, topotecan, gimatecan, irinotecan, camptothecan and its analogues, 9-nitrocamptothecin and the macromolecular camptothecin conjugate PNU-166148 (compound A1 in WO9917804); 10-hydroxycamptothecin acetate salt; etoposide; idarubicin hydrochloride; irinotecan hydrochloride; teniposide; topotecan, topotecan hydrochloride; doxorubicin; epirubicin, epirubicin hydrochloride; mitoxantrone, mitoxantrone hydrochloride; daunorubicin, daunorubicin hydrochloride, dasatinib (BMS-354825). Irinotecan can be administered, e.g., in the form as it is marketed, e.g., under the trademark CAMPTOSAR®. Topotecan can be administered, e.g., in the form as it is marketed, e.g., under the trademark HYCAMTIN®. The term "topoisomerase II inhibitor", as used herein, includes, but is not limited to, the anthracyclines, such as doxorubicin, including liposomal formulation, e.g., CAELYX®, daunorubicin, including liposomal formulation, e.g., DAUNOSOME®, epirubicin, idarubicin and nemorubicin; the anthraquinones mitoxantrone and losoxantrone; and the podophillotoxines etoposide and teniposide. Etoposide is marketed as ETOPOPHOS®; teniposide as VM 26-BRISTOL®; doxorubicin as ADRIBLASTIN® or ADRIAMYCIN®; epirubicin as FARMORUBICIN® idarubicin as ZAVEDOS®; and mitoxantrone as NOVANTRON®.

lxii. VEGFR tyrosine kinase inhibitor; which targets, decreases and/or inhibits the known angiogenic growth factors and cytokines implicated in the modulation of normal and pathological angiogenesis. The VEGF family (VEGF-A, VEGF-B, VEGF-C, VEGF-D) and their corresponding receptor tyrosine kinases [VEGFR-1 (Flt-1), VEGFR-2 (Flk-1, KDR), and VEGFR-3 (Flt-4)] play a paramount and indispensable role in regulating the multiple facets of the angiogenic and lymphangiogenic processes. An example of a VEGFR tyrosine kinase inhibitor includes 3-(4-dimethylaminobenzylidenyl)-2-indolinone. Compounds which target, decrease or inhibit the activity of VEGFR are especially compounds, proteins or antibodies which inhibit the VEGF receptor tyrosine kinase, inhibit a VEGF receptor or bind to VEGF, and are in particular those compounds, proteins or monoclonal antibodies generically and specifically disclosed in WO9835958, e.g. 1-(4-chloroanilino)-4-(4-pyridylmethyl)phthalazine or a pharmaceutical acceptable salt thereof, e.g. the succinate, or in WO0009495, WO0027820, WO0059509, WO9811223, WO0027819 and EP0769947; e.g. those as described by M. Prewett et al in Cancer Research 59 (1999) 5209-5218, by F. Yuan et al in Proc. Natl. Acad. Sci. USA, vol. 93, pp. 14765-14770, December 1996, by Z. Zhu et al in Cancer Res. 58, 1998, 3209-3214, and by J. Mordenti et al in Toxicologic Pathology, Vol. 27, no. 1, pp 14-21, 1999; in WO0037502 and WO9410202; Angiostatin, described by M. S. O'Reilly et al, Cell 79, 1994, 315-328; Endostatin described by M. S. O'Reilly et al, Cell 88, 1997, 277-285; anthranilic acid amides; ZD4190; ZD6474; SU5416; SU6668; or anti-VEGF antibodies or anti-VEGF receptor antibodies, e.g. RhuMab (bevacizumab). By antibody is meant intact monoclonal antibodies, polyclonal antibodies, multispecific antibodies formed from at least 2 intact antibodies, and antibodies fragments so long as they exhibit the desired biological activity. an example of an VEGF-R2 inhibitor e.g. includes axitinib, lxiii. a gonadorelin agonist, such as abarelix, goserelin, goserelin acetate, lxiv. a compound which induce cell differentiation processes, such as retinoic acid, alpha-, gamma- or 8-tocopherol or alpha-, gamma- or 8-tocotrienol.

lxv. a bisphosphonate, e.g. including etridonic, clodronic, tiludronic, pamidronic, alendronic, ibandronic, risedronic and zoledronic acid.

lxvi. a heparanase inhibitor which prevents heparan sulphate degradation, e.g. PI-88, lxvii. a biological response modifier, preferably alymphokine or interferons, e.g. interferon alpha, lxviii. a telomerase inhibitor, e.g. telomestatin, lxix. mediators, such as inhibitors of catechol-O-methyltransferase, e.g. entacapone, lxx. ispinesib, permetrexed (Alimta®), sunitinib (SU11248), diethylstilbestrol (DES), BMS224818 (LEA29Y), lxxi somatostatin or a somatostatin analogue, such as octreotide (Sandostatine or Sandostatin LAR®).

lxxii. Growth Hormone-Receptor Antagonists, such as pegvisomant, filgrastim or pegfilgrastim, or interferon alpha.

Cancer treatment, such as endocrine tumor treatment with an mTOR inhibitor, optionally in combination with an anticancer drug, such as indicated herein, may be associated with radiotherapy. Edocrine tumor treatment with an mTOR inhibitor, optionally in combination with an anticancer drug, may be a second line treatment, e.g. following treatment with another anticancer drug.

A preferred anticancer drug as a second drug substance in endocrine tumor treatment e.g. includes 5-fluorouracil, dacarbazine, streptozotocin, a receptor tyrosine kinase inhibitor that has a spectrum of activity that includes PDGFR, C-kit, and the VEGF receptor, e.g. SU011248, growth Hormone-Receptor Antagonists, such as pegvisomant, filgrastim or pegfilgrastim, interferon alpha or somatostatin or a somatostatin analogue, such as octreotide.

Preferably a second drug substance is somatostatin or a somatostatin analogue, such as octreotide, sold under the trade name Sandostatin® or Sandostatin LAR®.

Anti-inflammatory and/or immunomodulatory drugs which are prone to be useful in combination with an mTOR inhibitor e.g. prone to be useful according to the present invention, e.g. include mediators, e.g. inhibitors, of calcineurin, e.g. cyclosporin A, FK 506;

ascomycins having immuno-suppressive properties, e.g. ABT-281, ASM981;

corticosteroids; cyclophosphamide; azathioprene; leflunomide; mizoribine;

mycophenolic acid or salt; e.g. sodium, mycophenolate mofetil;

15-deoxyspergualine or an immunosuppressive homologue, analogue or derivative thereof;

mediators, e.g. inhibitors, of bcr-abl tyrosine kinase activity;

mediators, e.g. inhibitors, of c-kit receptor tyrosine kinase activity;

mediators, e.g. inhibitors, of PDGF receptor tyrosine kinase activity, e.g. Gleevec (imatinib);

mediators, e.g. inhibitors, of p38 MAP kinase activity, mediators, e.g. inhibitors, of VEGF receptor tyrosine kinase activity, mediators, e.g. inhibitors, of PKC activity, e.g. as disclosed in WO0238561 or WO0382859, e.g. the compound of Example 56 or 70;

mediators, e.g. inhibitors, of JAK3 kinase activity, e.g. N-benzyl-3,4-dihydroxy-benzylidene-cyanoacetamide α-cyano-(3,4-dihydroxy)-]N-benzylcinnamamide (Tyrphostin AG 490), prodigiosin 25-C(PNU156804), [4-(4'-hydroxyphenyl)-amino-6,7-dimethoxyquinazoline] (WHI-P131), [4-(3'-bromo-4'-hydroxylphenyl)-amino-6,7-dimethoxyquinazoline] (WHI-P154), [4-(3',5'-di-bromo-4'-hydroxylphenyl)-amino-6,7-dimethoxy-yquinazoline] WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690,550), or a compound as disclosed in WO2004052359 or WO2005066156;

mediators, e.g. agonists or modulators of S1P receptor activity, e.g. FTY720 optionally phosphorylated or an analog thereof, e.g. 2-amino-2-[4-(3-benzyloxyphenylthio)-2-chlorophenyl]ethyl-1,3-propanediol optionally phosphorylated or 1-{4-[1-(4-cyclohexyl-3-trifluoromethyl-benzyloxyimino)-ethyl]-2-ethyl-benzyl}-azetidine-3-carboxylic acid or its pharmaceutically acceptable salts;

immunosuppressive monoclonal antibodies, e.g., monoclonal antibodies to leukocyte receptors, e.g., Blys/BAFF receptor, MHC, CD2, CD3, CD4, CD7, CD8, CD25, CD28, CD40, CD45, CD52, CD58, CD80, CD86, IL-12 receptor, IL-17 receptor, IL-23 receptor or their ligands;

other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y;

mediators, e.g. inhibitors of adhesion molecule activities, e.g. LFA-1 antagonists, ICAM-1 or -3 antagonists, VCAM-4 antagonists or VLA-4 antagonists, mediators, e.g. antagonists of CCR9 activity, mediators, e.g. inhibitors, of MIF activity, 5-aminosalicylate (5-ASA) agents, such as sulfasalazine, Azulfidine®, Asacol®, Dipentum®, Pentasa®, Rowasa®, Canasa®, Colazal®, e.g. drugs containing mesalamine; e.g mesalazine in combination with heparin;

mediators, e.g. inhibitors, of TNF-alpha activity, e.g. including antibodies which bind to TNF-alpha, e.g. infliximab (Remicade®), thalidomide, lenalidomide, nitric oxide releasing non-steriodal anti-inflammatory drugs (NSAIDs), e.g. including COX-inhibiting NO-donating drugs (CINOD);

phosphordiesterase, e.g. mediators, such as inhibitors of PDE4B activity, mediators, e.g. inhibitors, of caspase activity, mediators, e.g. agonists, of the G protein coupled receptor GPBAR1, mediators, e.g. inhibitors, of ceramide kinase activity, 'multi-functional anti-inflammatory' drugs (MFAIDs), e.g. cytosolic phoshpholipase A2 (cPLA2) inhibitors, such as membrane-anchored phospholipase A2 inhibitors linked to glycosaminoglycans;

antibiotics, such as penicillins, cephalosporins, erythromycins, tetracyclines, sulfonamides, such as sulfadiazine, sulfisoxazole; sulfones, such as dapsone; pleuromutilins, fluoroquinolones, e.g. metronidazole, quinolones such as ciprofloxacin; levofloxacin; probiotics and commensal bacteria e.g. *Lactobacillus, Lactobacillus reuteri;* antiviral drugs, such as ribivirin, vidarabine, acyclovir, ganciclovir, zanamivir, oseltamivir phosphate, famciclovir, atazanavir, amantadine, didanosine, efavirenz, foscarnet, indinavir, lamivudine, nelfinavir, ritonavir, saquinavir, stavudine, valacyclovir, valganciclovir, zidovudine.

Anti-inflammatory drugs which are prone to be useful in combination with an mTOR inhibitor, e.g. prone to be useful according to the present invention, include e.g. non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); cyclooxygenase-2 (COX-2) inhibitors such as celecoxib; inhibitors of phosphodiesterase type IV (PDE-IV); antagonists of the chemokine receptors, especially CCR-1, CCR-2, and CCR-3; cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; anticholinergic agents such as muscarinic antagonists (ipratropium bromide); other compounds such as theophylline, sulfasalazine and aminosalicylates, e.g. 5-aminosalicylic acid and prodrugs thereof, antirheumatics.

Antiallergic drugs which are prone to be useful in combination with an mTOR inhibitor, e.g. prone to be useful according to the present invention, e.g. include antihistamines (H1-histamine antagonists), e.g. bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and non-steroidal anti-asthmatics such as β2-agonists (terbutaline, metaproterenol, fenoterol, isoetharine, albuterol, bitolterol, salmeterol and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); bronchodilators, antiasthmatics (mast cell stabilizers).

In each case where citations of patent applications or scientific publications are given, the subject-matter relating to the compounds is hereby incorporated into the present application by reference, e.g. comprised are likewise the pharmaceutical acceptable salts thereof, the corresponding racemates, diastereoisomers, enantiomers, tautomers as well as the corresponding crystal modifications of above disclosed compounds where present, e.g. solvates, hydrates and polymorphs, which are disclosed therein. The compounds used as active ingredients in the combinations of the invention may be prepared and administered as described in the cited documents or in the product description, respectively. Also within the scope of this invention is the combination of more than two separate active ingredients as set forth above, i.e. a pharmaceutical combination within the scope of this invention could include three active ingredients or more. Further, both the first agent and the co-agent are not the identical ingredient.

The structure of the drug substances identified by code numbers, generic or trade names may be taken from the Internet, actual edition of the standard compendium "The Merck Index" or from databases, e.g., Patents International, e.g., IMS World Publications, or the publications mentioned above and below. The corresponding content thereof is hereby incorporated by reference.

Utility of the mTOR inhibitors in treating endocrine tumors as hereinabove specified, may be demonstrated in vitro, in animal test methods as well as in clinic, for example in accordance with the methods hereinafter described.

A. In Vitro
A. 1 Antiproliferative Activity in Combination with Other Agents

A cell line, e.g. the Compound A resistant A549 line ($IC_{50}$ in low nM range) versus the comparative Compound A resistant KB-31 and HCT116 lines ($IC_{50}$ in the, micromolar range), is added to 96-well plates (1,500 cells/well in 100 ul medium) and incubated for 24 hr. Subsequently, a two-fold dilution series of each compound (an mTOR inhibitor other than Compound A or a known chemotherapeutic agent) is made in separate tubes (starting at 8× the $IC_{50}$ of each compound) either alone or in paired combinations, and the dilutions are added to the wells.

The cells are then re-incubated for 3 days. Methylene blue staining is performed on day 4 and the amount of bound dye (proportional to the number of surviving cells that bind the dye) determined. $IC_{50}$s are subsequently determined using the Calcusyn program, which provides a measure of the interaction, namely the so-called non-exclusive combination index (CI), where: CI~1=the interaction is nearly additive; 0.85-0.9=slight synergism; <0.85=synergy. In this assay, mTOR inhibitors, e.g. the compound A, show interesting antiproliferative activity in combination with another chemotherapeutic agent, e.g. such as defined above, e.g. in combination with somastatin or a somastatin analogue.

B. In Vitro Assay

The phosphorylation status of downstream markers S6 (the inhibition of S6K1 activity) is used as a read out, reflecting the immediate pharmacodynamic effect of the mTOR inhibitor, e.g. in the p70S6 kinase 1 (S6K1) assay, see e.g. WO2005064343.

Carcinoid efficacy may be determined by measurement of chromogranin A which is inter alia hypersecreted in carcinoid cells, see e.g. Davis et al, Gynecology & Obstetrics 1973; 137:637-644.

C. In Vitro Studies

Compound A is able to restore activity of endocrine agents, like estrogen inhibitors and/or aromatase inhibitors in cells which are otherwise resistant to endocrine agent treatment. Several studies have implicated aberrant activity of the Akt kinase as a significant mechanism by which breast cancer tumors are unresponsive to endocrine therapy.

D. Clinical Trials

In clinical trial studies involving patients having carcinoid or islet cell cancer inhibition of S6K1 activity and a reduction of chromogranin A may be observed when administering either Compound A alone, or a combination of Sandostatin LAR® (30 mg daily) and compound A (5 mg daily). Response evaluation may be performed every 12 weeks. Study duration: 6 months).

Also synergistic effects of such combination are obtained.

Further clinical studies using Compound A in an amount of 5 mg or 10 mg daily (5 to 70 mg weekly) in monotherapy, and in combination therapy together with, e.g. 30 mg, of Sandostatin LAR® daily are investigated, e.g.

A randomized, double-blind, placebo controlled study of compound A in 420 patients who are receiving therapy with Sandostatin LAR® for advanced midgut carcinoid tumors. Patients continue baseline Sandostatin LAR® therapy and are randomized to receive Compound A 10 mg/day or placebo. Primary endpoint is progression free survival (PFS). Secondary endpoints include overall survival, carcinoid-associated symptoms of flushing and diarrhea, pharmakinetics and pharmadynamics. For efficacy assessment progression and response are assessed per RECIST criteria. Due to the nature of neuroendocrine tumors, all patients must have triphasic CT scans or MRI. Scans are repeated every two months. Aim: Compound A in combination with Sandostatin LAR® for treatment of advanced progressing midgut tumor (carcinoid tumor).

A single-arm placebo controlled study of Compound A 10 mg/day in 100 patients with measurable advanced (metastatic or unresentable) pancreatic neuroendcrine tumors (islet cell tumor) after failure of cytotxic chemotherapy as a monotherapy. Primary goal is to determine the response rate. A cohort of 44 patients receiving chronic treatment with Sandostain LAR® for secretory pancreatic tumors are also be treated with Compound A, 10 mg a day, in addition to Sandostatin LAR®.

The invention claimed is:
1. A method for treating pancreatic neuroendocrine tumors, comprising administering to a human subject in need thereof a therapeutically effective amount of 40-O-(2-hydroxyethyl)-rapamycin as a monotherapy and wherein the tumors are advanced tumors after failure of cytotoxic chemotherapy.

2. The method of claim 1, wherein a unit dose of 40-O-(2-hydroxyethyl)-rapamycin is 10 mg/day.

3. The method of claim 1, wherein the tumor is islet cell tumor.

* * * * *

(12) INTER PARTES REVIEW CERTIFICATE (2299th)
United States Patent
Marks et al.

(10) Number: US 9,006,224 K1
(45) Certificate Issued: Aug. 23, 2021

(54) NEUROENDOCRINE TUMOR TREATMENT

(75) Inventors: Peter Wayne Marks; David Lebwohl

(73) Assignee: NOVARTIS AG

Trial Numbers:

IPR2017-01063 filed Mar. 10, 2017
IPR2016-01479 filed Jul. 22, 2016

Inter Partes Review Certificate for:

Patent No.: 9,006,224
Issued: Apr. 14, 2015
Appl. No.: 12/094,173
Filed: May 19, 2008

The results of IPR2017-01063 joined with IPR2016-01479 are reflected in this inter partes review certificate under 35 U.S.C. 318(b).

INTER PARTES REVIEW CERTIFICATE
U.S. Patent 9,006,224 K1
Trial No. IPR2017-01063
Certificate Issued Aug. 23, 2021

AS A RESULT OF THE INTER PARTES REVIEW PROCEEDING, IT HAS BEEN DETERMINED THAT:

Claims 1-3 are found patentable.

\* \* \* \* \*